United States Patent [19]

Crawford et al.

[11] Patent Number: 5,114,678

[45] Date of Patent: May 19, 1992

[54] DEVICE FOR WIPING A REAGENT STRIP

[75] Inventors: Ferdon H. Crawford, Elkhart; Gabriel R. Shakour, South Bend; Robert C. Whitson, Osceola; Ernest R. Wise, Elkhart, all of Ind.

[73] Assignee: Miles Inc., Elkhart, Ind.

[21] Appl. No.: 496,691

[22] Filed: Mar. 21, 1990

[51] Int. Cl.⁵ .............................................. B01L 11/00
[52] U.S. Cl. ...................................... 422/99; 422/58; 422/61; 422/104; 435/294; 436/66
[58] Field of Search ................. 422/58, 61, 99, 104; 435/294; 436/66

[56] References Cited

U.S. PATENT DOCUMENTS

| | | | |
|---|---|---|---|
| 3,966,552 | 6/1976 | Pagano et al. | 435/294 |
| 4,963,325 | 10/1990 | Lennon et al. | 422/61 |
| 5,004,584 | 4/1991 | Rayman | 436/66 |

Primary Examiner—Robert J. Warden
Assistant Examiner—Laura E. Collins
Attorney, Agent, or Firm—Roger N. Coe

[57] ABSTRACT

The removal of excess fluid from a test strip should be performed in a consistent manner to provide consistent results. To eliminate user variability introduced by manual blotting techniques, the device of the present invention wipes fluid from a test strip as the test strip is passed beneath a blade. The one-piece device is made of plastic so that it may be manufactured inexpensively and disposed of after use. The wiping device can also be integrated with an end cap, so that the wiping device can be attached to the end of an instrument, such as a lancet. To obtain a blood sample, for instance, the user inserts a test strip into the wiping device, where it is held while the blood sample is taken. The user deposits the blood sample onto the test strip and pulls the test strip through the wiping device. The blade removes a portion of the blood sample to provide a consistent wiping action which is not influenced by user variability. Alternative embodiments of the wiping device include apertures for viewing the test strip after wiping and colors adjacent the apertures for comparing the color of a reagent pad on the test strip after interaction with the body fluid.

5 Claims, 3 Drawing Sheets

U.S. Patent  May 19, 1992  Sheet 1 of 3  5,114,678
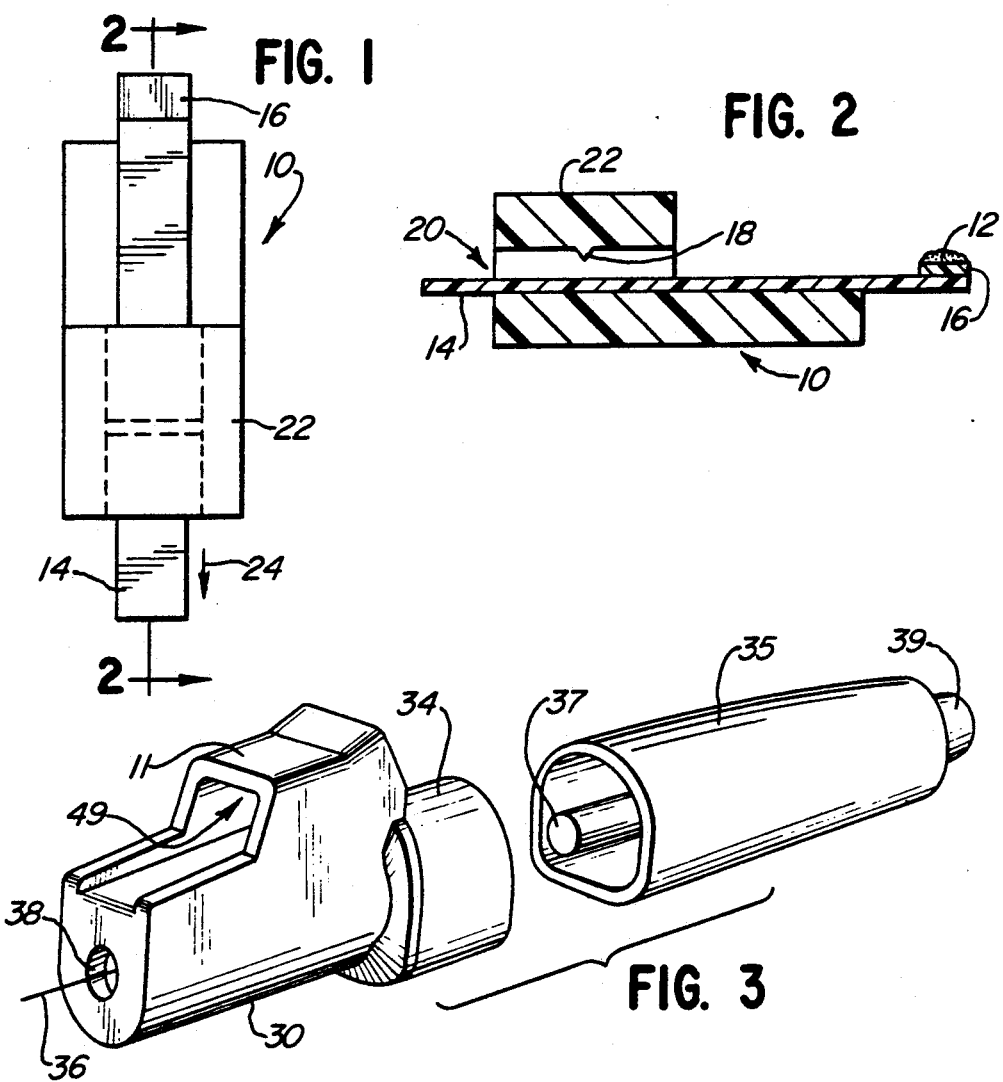
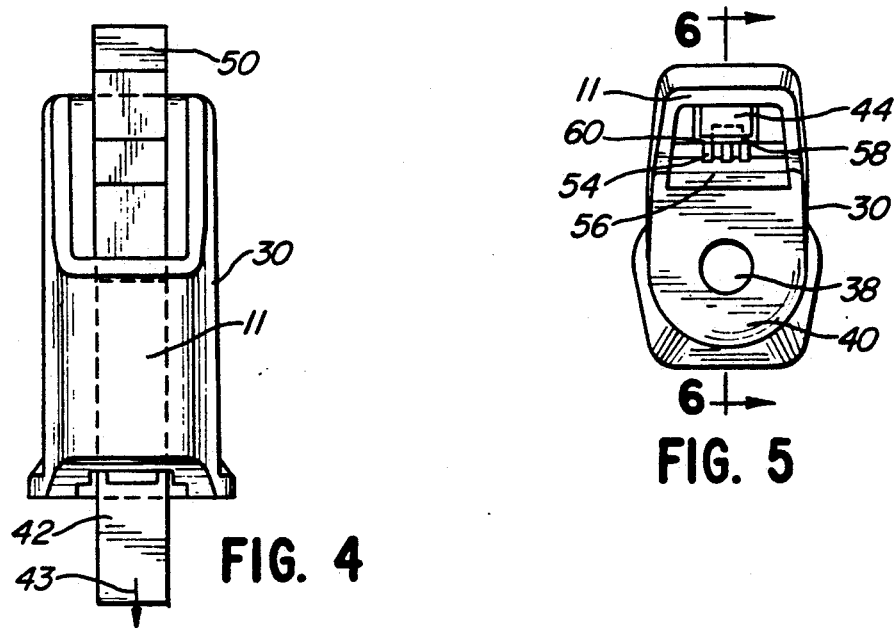

DEVICE FOR WIPING A REAGENT STRIP

BACKGROUND OF THE INVENTION

1. Field of the Invention

The present invention relates generally to blood glucose testing, and more particularly to a device which consistently wipes blood from a reagent strip, thus eliminating user variations and providing reliable test results.

2. Description of Related Art

Blood glucose testing is an important part of life for people afflicted with diabetes. Diabetics must monitor their blood glucose levels periodically to avoid complications caused by excessive levels of glucose in the blood. Although many diabetics received regular insulin injections which reduce the blood glucose level, blood glucose levels can still vary widely. The reason for this wide variation is that the regular insulin injections are not necessarily proportional to the blood glucose level. If a diabetic has ingested foods which raise the blood glucose level, the insulin present in his body may not be sufficient to return his blood glucose level to normal. Conversely, a diabetic may have a low blood glucose level caused by too much insulin in his system. Therefore, diabetics monitor their blood glucose levels periodically so that they may alter their ingestion of certain foods to either raise or lower their blood glucose level as needed. Sustained high or low levels of blood glucose may be an indication that the amount of insulin prescribed is either too low or too high, respectively.

Reagent strips are typically used to determine the blood glucose level in a sample of a diabetic's blood. The reagent strips are generally plastic strips which have a reagent pad on one end thereof. Chemicals on the reagent pad react with glucose to provide an indication of the concentration of glucose in the blood. The glucose in the blood sample causes the reagent pad to change color, and the resulting color is an indication of the concentration of glucose in the patient's blood. Typically, a sample of the diabetic's blood is placed on the reagent pad for a predetermined amount of time, and then the excess blood is wiped off to reveal the color of the reagent pad. The color of the reagent pad is then compared to a number of color standards which correspond to specific blood glucose level ranges. Alternatively, the reagent pads are inserted into a device, such a reflectance photometer, which more accurately determines the concentration of glucose in the blood sample on the reagent strip.

The accuracy of blood glucose testing of this type is affected by several factors. First, the blood sample should be left on the reagent pad for the predetermined amount of time. A longer or shorter time will affect the absorption of the blood into the reagent pad, and thus affect the resulting color of the reagent pad. Second, the wiping process which removes the blood after the predetermined amount of time can affect the resulting color of the reagent pad. If the method for wiping the blood off of the reagent pad is inconsistent, the blood glucose concentration indicated by the reagent pad will also be inconsistent. While the first problem can be substantially overcome by stressing the importance of accurately monitoring the amount of time that the blood sample remains on the reagent strip, the second problem can not be easily overcome merely through education of diabetic patients.

Current methods to remove the excess blood from the reagent strip include blotting or rubbing the reagent strip with tissues or another absorbent material while the reagent strip is place on a flat, hard surface. This method of blood removal requires a high degree of user technique and introduces a high level of user variability. Moreover, this type of blotting technique tends to smear or spread the blood.

In an attempt to produce consistent results and a controlled wiping action, Hyproguard LTD of Dock Lane, Woodbridge, Suffolk, U.K. is currently manufacturing a wiping device referred to as HY-GUARD. The HY-GUARD device is a disposable plastic device which accepts the blood sample into a capillary gap in the device which transports the blood to a reagent pad. Upon withdrawal, the reagent pad passes beneath an absorbent wiping material which removes excess blood from the reagent pad. While the HY-GUARD device provides consistent results as compared with the variability introduced by manual wiping, the absorbency of the wiping material can introduce inconsistencies during the wiping action. Moreover, the manufacture of the HY-GUARD device is complicated in that two molded parts must be assembled and the absorbent material must be attached thereto.

SUMMARY OF THE INVENTION

It is an object of the present invention to provide a wiping device which provides consistent results.

It is a further object of the present invention to provide a disposable, one-piece wiping device.

It is another object of the present invention to provide a conveniently located wiping device.

It is yet another object of the present invention to provide a wiping device which is inexpensive to manufacture and easy to assemble.

It is still another object of the present invention to provide a wiping device which does not use absorbent material.

It is a still further object of the present invention to provide a wiping device which may be disposed of after use.

The wiping device of the present invention squeegees or wipes fluid, such as a blood sample, off of a test strip. In accordance with one aspect of the present invention, a wiping device of this type is provided with a housing which has an aperture extending therethrough. The aperture is dimensioned to allow a test strip to be pulled through the housing. A squeegee bar or blade extends into the aperture to contact the fluid on the test strip as the test strip passes beneath the bar or blade. The bar or blade is located relative to the test strip so that excess fluid is removed from every test strip to provide consistent results independent of user technique.

For user convenience, one embodiment of the wiping device of the present invention is formed into an end cap which can be attached to end of a lancet. A flexible squeegee bar or blade extends into an aperture which extends through a portion of the end cap. A blood testing strip is held within the aperture. The user may then obtain a blood sample with the lancet, and apply the blood sample directly to the reagent pad on the blood testing strip which is being held in the end cap. After a predetermined amount of time, the blood testing strip is pulled through the aperture, and the squeegee bar or blade wipes a portion of the blood sample off of the reagent pad as the reagent pad passes beneath the bar or blade. This technique consistently leaves a predetermined amount of the blood sample on the reagent pad, thus providing consistent test results.

As a further advantage, the wiping device is formed into a one-piece plastic unit which can be disposed of after use. Moreover, reservoirs or channels within the wiping device tend to hold the removed portion of the blood sample within the device to prevent contamination caused by contact with the blood.

Other embodiments of the present invention include a jacket or envelope with at least one viewing aperture. A test strip is mounted in the envelope with a reagent pad on the test strip extending out of the envelope. A user deposits body fluid onto the reagent pad. After the elapse of a predetermined time, the user pulls the reagent pad into the envelope. The body fluid on the reagent pad is spread over the pad and excess fluid is wiped off the pad by wiper ribs formed on the inside of the envelope. The reagent pad is pulled to the viewing aperture, and the color of the reagent pad is read by an instrument or visually compared to a color chart or wheel printed on the envelope adjacent the viewing aperture.

BRIEF DESCRIPTION OF THE DRAWINGS

Other objects and advantages of the invention will become apparent upon reading the following detailed description and upon reference to the drawings in which:

FIG. 1 is a top plan view of a wiping device constructed in accordance with the present invention;

FIG. 2 is a sectional view taken along line 2—2 in FIG. 1;

FIG. 3 is a perspective view of an end cap wiping device constructed in accordance with the present invention illustrated with other components;

FIG. 4 is a top plan view of the end cap wiping device of FIG. 3;

FIG. 5 is a front plan view of the end cap wiping device of FIG. 3;

Figure 6:
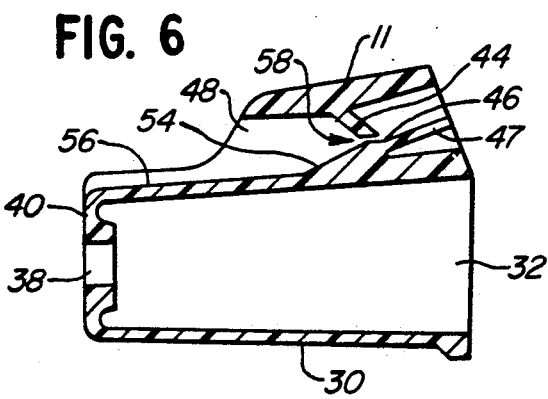
FIG. 6 is a sectional view taken along line 6—6 in FIG. 5.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Turning now to the drawings and referring initially to FIGS. 1 and 2, a wiping device 10 is used to remove a fluid sample 12 from a test strip 14. The test strip 14 includes a chemically treated reagent pad 16 on which the fluid sample 12 is placed. The blood sample 12 is placed on the reagent pad 16 for a predetermined amount of time, during which time the glucose in the blood sample reacts with chemicals on the reagent pad 16. This chemical interaction causes the color of the reagent pad 16 to change, and the resulting color indicates the concentration of glucose in the blood sample. It is to be noted that analytes other than glucose can be detected using the test strip 14, and glucose is discussed herein merely as an illustrative example. In addition, body fluids other than blood, such as urine or saliva, can be tested using the test strip 14. These features of the discussion herein are merely for illustrative purposes and are not intended to limit the invention.

After the blood sample 12 has remained on the reagent pad 16 for the predetermined amount of time, it is important that the blood sample 12 be wiped off of the reagent pad 16 in order to determine the color of the reagent pad 16. To wipe the blood sample 12 off of the reagent pad 16, the device 10 uses a squeegee bar 18. The squeegee bar 18 and the other wiping structures discussed herein can be any useable material and preferably is a soft plastic such as a low density polyethylene. The squeegee bar 18 extends into an aperture 20. The aperture 20 extends through the housing 22, and is dimensioned to allow the test strip 14 to be longitudinally inserted into the aperture 20. The test strip 14 is pulled through the aperture 20 in the direction of the arrow 24 (FIG. 1). The squeegee bar 18 comes into contact with the blood sample 12 as the reagent pad 16 passes beneath the squeegee bar 18, and, thus, wipes a portion of the blood sample 12 off of the reagent pad 16.

The wiping device 10 is preferably a one-piece plastic part made by an injection molding process. Since plastic is inexpensive and a one-piece part does not require an assembly process, the overall cost of the wiping device 10 is low. Therefore, once the wiping device 10 has been used and contaminated with blood, it may be disposed of in a proper manner.

For the convenience of the users, a wiping device 11 may be incorporated into an end cap 30, as shown in FIGS. 3-8. The end cap 30 includes a hollow cavity 32 which is dimensioned to fit on a selected tubular member, such as a lancet 34. A user obtains a blood sample by using a needle 36 of the lancet 34 to open a small wound. Preferably, a base unit 35, which includes a spring-loaded hammer 37, connects to one end of the lancet 34. When the spring-loaded hammer 37 is actuated by depressing a button 39, the needle 36 is driven into the user's finger. Prior to obtaining the blood sample, the end cap 30 is placed over one end of the lancet 34. Preferably, the end cap 30 includes an opening 38 which extends through the front portion 40 of the end cap 30 into the hollow cavity 32. The opening 38 allows the end cap 30 to be placed on the lancet 34, so that the needle 36 protrudes through the opening 38. While the foregoing describes an end cap 30 which is placed over the end of the lancet 34, it is often preferable to form the wiping device 11 integral with the lancet 34. Since a lancet is typically disposed of after obtaining a blood sample, a wiping device formed thereon provides additional convenience.

The wiping device 11 uses a squeegee blade 44 to wipe the blood sample 52 off of the reagent pad 50. The squeegee blade 44 extends into an aperture 48. The aperture 48 extends through a portion of the end cap 30, and is dimensioned to allow the test strip 42 to be longitudinally inserted into the aperture 48. As the test strip 42 is pulled through the aperture 48 in the direction of the arrow 43 (FIG. 4), the squeegee blade 44 comes into contact with the blood sample 52 as the reagent pad 50 passes beneath the squeegee blade 44 (FIG. 8) and wipes a portion of the blood sample 52 off of the reagent pad 50.

To further enhance the convenience of the end cap 30, the integral wiping device 11 holds the test strip 42 while the lancet 34 is used to obtain a blood sample. The space between the squeegee blade 44 and a guiding surface 46 is dimensioned so that an inserted test strip is held therebetween. Preferably, the squeegee blade 44 is a thin plastic blade which is integral with the wiping device 11. The squeegee blade 44 is resilient so that when it contacts the test strip 42 it bends in the direction of motion of the test strip 42. When the test strip 42 has been inserted into the aperture 48 such that it is positioned to accept a blood sample on the reagent pad 50, the resilient squeegee blade 44 applies a small amount of pressure to the test strip 42 to hold it in place while the user obtains a blood sample with the lancet 34. However, if the desired interference between the squeegee blade 44 and the guiding surface 46 does not allow the test strip 42 to be held therebetween, a tab 47 is used to bend the test strip 42 slightly toward the squeegee blade 44. The pressure applied to the test strip 42 by the tab 47 holds the test strip 42 within the integral wiping device 11 so that the test strip 42 will not fall out of the integral wiping device during the use of the lancet 34.

To allow the test strip 42 to be inserted into the wiping device 11 easily, guide ramps 54 slope upwardly toward the squeegee blade 44 to progressively narrow the aperture 48. Since a test strip 42 is typically made of a thin plastic material, it is desirable that the test strip 42 is placed on a flat surface to provide a stable surface and to prevent the end of the strip from moving while the user attempts to place a blood sample onto the reagent pad 50. Therefore, a flat surface 56 of the wiping device 11 leads to the ramps 54, and allows the user to conveniently deposit the blood sample onto the reagent pad 50. Since a blood sample is typically taken from the users finger, a user presses his finger onto the reagent pad 50 which is supported by the surface 56.

Another advantage of the guide ramps 54 is that excess blood which has been wiped off of the reagent pad 50 falls into channels 60, which are formed between the ramps 54, and is thereby retained within the wiping device 11. Since the blood is retained within the wiping device 11, the end cap 30 may be disposed of without blood contaminating anything other than the end cap 30. This is extremely advantageous to medical personnel who could quite easily be contaminated by a patient's blood in the absence of a means for retaining blood within the wiping device 11.

Figure 7:
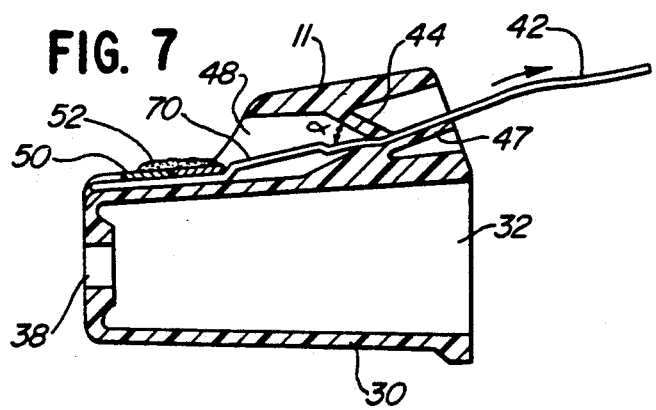
FIG. 7 is the sectional view of FIG. 6 which includes a test strip being held within the wiping device.

The squeegee blade 44 is preferably angled to extend generally in the direction of motion of the test strip. As can be seen in reference to FIG. 6, the combination of the angled squeegee blade 44 and the upwardly sloping ramps 54 narrow the aperture 48 to form a slit 58 between the squeegee blade 44 and the surface 46. The narrowing aperture 48 allows the test strip 42 to be inserted beneath the squeegee blade 44 with ease. The angled squeegee blade 44 also uniformly removes excess blood from the reagent pad 50, and spreads blood evenly over the reagent pad 50, since the blade 44 provides a smooth wiping action. Moreover, it should be kept in mind that the reagent pad 50 should not be damaged by the wiping action. The spacing between the squeegee blade 44 and the surface 46 is preferably about 0.003–0.005 inch (0.0076–0.0127 cm) less than the height of the reagent pad 50. Since the squeegee blade 44 not only contacts the fluid but also contacts the reagent pad 50, the smooth wiping action provided by the angle of the squeegee blade 44 does not tear into or rip the reagent pad 50 as the strip 42 is pulled through the wiping device 10. It has been found that an angle, as shown in FIG. 7, of about 50° to 60° between the squeegee blade 44 and the test strip 42 provides adequate wiping action and does not damage the reagent pad 50.

To further protect the reagent pad 50 from damage, the test strip 42 may include a raised portion 70 which raises the squeegee blade 44 up to the level of the reagent pad 50. As the test strip 42 is pulled through the wiping device 10, the squeegee blade 44 rides up on the raised portion 70 instead of riding up on the edge of the reagent pad 50. This prevents the squeegee blade 44 from possibly tearing the edge of the reagent pad 50, or from possibly removing the reagent pad 50 from the test strip 42.

Figure 9:
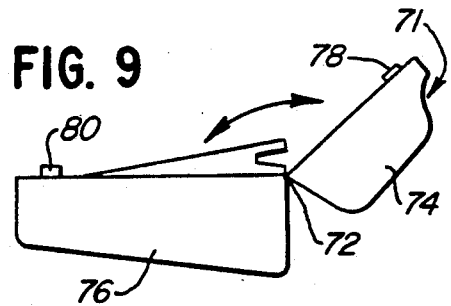
FIG. 9 is an alternate embodiment of a wiping device constructed in accordance with the present invention.

Refer now to FIG. 9, wherein an alternative wiping device 71 is illustrated. Should the user wish to reuse the wiping device 71, the contaminating blood needs to be cleaned therefrom. To facilitate the cleaning process, the wiping device 71 is provided with a hinge 72 which allows a top portion 74 of the wiping device 71 to pivot with respect to a base portion 76 of the wiping device 71. The pivotal portions allow internal portions of the wiping device 71 to be cleaned. After the blood has been thoroughly cleaned from the internal portions of the wiping device 71, the top portion 74 is secured to the base portion 76 by means of plastic snaps 78, 80 which are formed integrally with the plastic wiping device 71.

Figure 10:
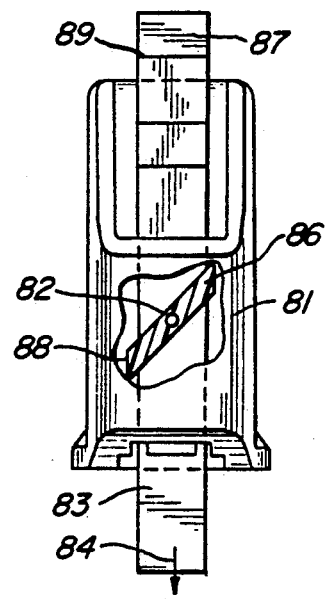
FIG. 10 is an alternate embodiment of a wiping device constructed in accordance with the present invention.
Figure 8:
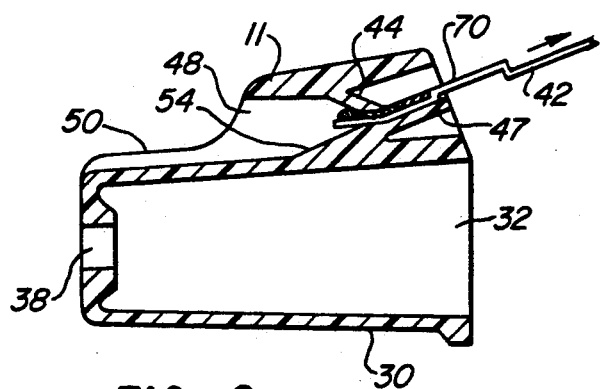
FIG. 8 is the sectional view of FIG. 6 which includes a test strip positioned with the reagent pad passing beneath the blade of the wiping device.

The embodiments shown thus far incorporate a squeegee bar 18 or blade 44 which form an angle of incidence with the test strip 14 or 42 of 90° or less, and which form an angle of 90° with respect to the direction of motion of the test strip 14,42. However, a squeegee blade 82 which is angled with respect to the direction of motion of a test strip 83 effectively removes blood from the test strip 83 with consistency. FIG. 10 illustrates a top view of a wiping device 81 which includes a squeegee bar 82 that forms an angle of incidence with the test strip 83 of 90° or less, and is angled relative to the direction of motion of the test strip 83, so that the angle is less than 90°. As the test strip 83 is pulled through the wiping device 81 in the direction of the arrow 84, the leading edge 86 of the squeegee bar 82 begins to remove a portion of the blood sample 87 from the reagent pad 89. The squeegee bar 82 continues to wipe blood from the reagent pad 89 by forcing the blood along the squeegee bar 82 towards the trailing edge 88.

Figure 11:
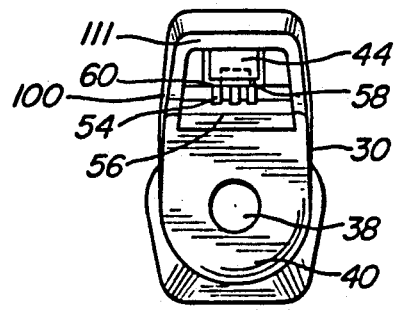
FIG. 11 is a view similar to FIG. 6 illustrating an alternative embodiment of a wiping device including a side slit for insertion of a test strip.

Turning to FIG. 11, there is illustrated a wiping device 111 that is similar to the wiping device 11. Components of the wiping device 111 that are identical to the corresponding components of the wiping device 11 are identified by the same reference numerals. The wiping device 111 differs from the wiping device 11 in that the wiping device 111 allows side insertion of the test strips 14. A slit 100 is formed in the end cap 30 and extends along the length of the end cap. A user by holding the handle of a test strip 14, can insert the pad 16 of the test strip 14 into the aperture 48. The handle of the test strip 14 can then be moved forwardly of the cap 30 along the length of the slit 100 to wipe the pad 16 by the squeegee blade 44. This side insertion of the reagent strip allows easy loading of the strip 14 since the user can hold the handle of the strip 14 while wiping the pad 16 rather than having to grasp the reagent pad side of the strip 14 to load or pull the strip 14 through the wiping device.

In summary, a wiping device having a squeegee bar or blade consistently removes excess blood from a test strip to eliminate the user variation which arises from blotting techniques. Since the test strips are consistently wiped, the test strips provide consistent and more accurate indications of analytic levels. For additional user convenience, the wiping device is formed integrally with an end cap or a lancet, so that the wiping device holds the test strip while the user obtains a blood sample. After the test strip is wiped, the excess blood remains within the wiping device to prevent contamination, and the one-piece, plastic wiping device is then disposed.

Figure 12:
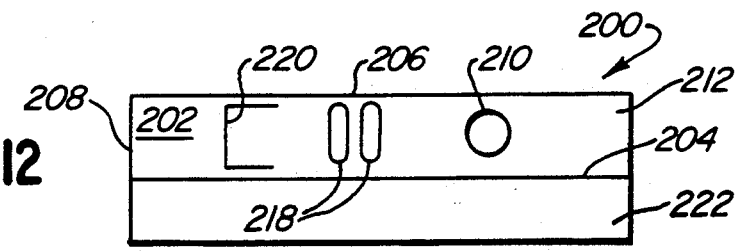
FIG. 12 is a top plan view of a first alternative embodiment of an unassembled wiping device that is self-contained to allow wiping and reading of a reagent pad in the same device.
Figure 13:
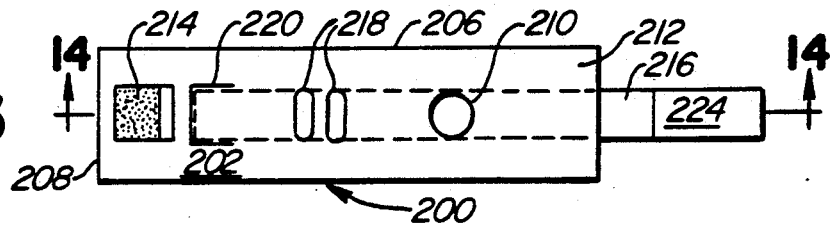
FIG. 13 is an enlarged, top plan view of the wiping device illustrated in FIG. 12 as assembled.
Figure 14:
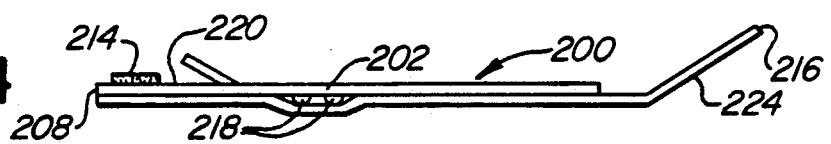
FIG. 14 is a vertical cross section view taken generally along line 14—14 in FIG. 13.

Turning now to FIGS. 12-14, there is illustrated a disposable wiping device generally designated by the reference numeral 200. The wiping device 200 consists of a flat sheet of flexible material 202 such as Trycite. The sheet 202 forms an envelope 203 by folding it in half along a fold line 204 and sealing it along a side edge 206 and along the edge of a forward end 208. Prior to the assembly of the wiping device 200, a viewing aperture 210 is cut or otherwise formed in a top layer 212 sheet of flexible material 202.

During the formation of the envelope 203, a test or reagent strip 216 is positioned in an interior cavity formed in the envelope 203. A reagent pad 214 is secured to the reagent strip 216. The reagent pad 214 extends out of the interior cavity through a slot 220 cut in the top layer 212 of the material 202.

To determine the level of an analyte in a body fluid, a drop of body fluid is placed on the reagent pad 214. After the expiration of a predetermined period of time, the body fluid is spread over the reagent pad and the excess is wiped off by wiper ribs 218 formed on the underside of top layer 212 and extending into the interior cavity of the envelope 203. This is accomplished by the user pulling the reagent strip 216 to pull the pad 214 through the slot 220 and into the cavity of the envelope 203.

Users of a reagent strip must wipe or blot a reagent pad on the strip after the deposit of a body fluid such as blood on the reagent pad. After blotting or wiping, the reagent pad is read, either visually or by matching a color chart, to determine the content of an analyte in the body fluid. This reading is sensitive to the technique of blotting or wiping that is used, and a different technique can change the readings. For example, the readings can be changed depending on the type of tissue paper or blotting paper used, how much pressure is applied, and how many times the user blots the reagent pad.

The wiping device 200 controls all of these uncontrollable features by providing a predetermined pressure for wiping. The design of the wiping device 200 also determines how many wipings occur, and this number of wipings is constant for each wiping device 200. In addition, the wiping device 200 is easily disposed of without the concern of contamination.

To use the wiping device 200, a user deposits a body fluid such as blood on the reagent pad 214. After a predetermined period of time has elapsed, the handle portion 224 of the reagent strip 216 is grasped and pulled to move the reagent pad 214 through the slot 220 and into the cavity between the top layer 212 and the bottom layer 222 of the wiping device 200. Continued rearward movement or pulling of the reagent strip 216 wipes the top surface of the reagent pad 214 across the wiper ribs 218. Excess fluid is wiped off the reagent pad 214 and safely contained in the interior cavity of the envelope 203. Further pulling of the reagent strip 216 positions the reagent pad 214 within the viewing aperture 210. The user can then read the color of the reagent pad 214 visually or use an instrument specially designed to read the color of the reagent pad 214. Once the reading is completed, the user may dispose of the entire wiping device 200 thus avoiding possible contamination.

Figure 15:
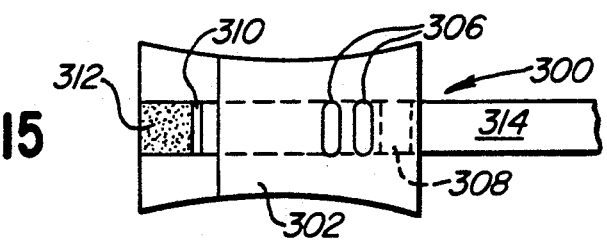
FIG. 15 is top plan view of a second alternative embodiment of a wiping device.
Figure 16:
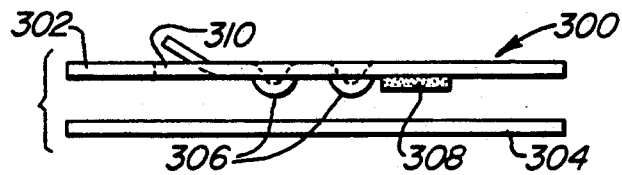
FIG. 16 is an enlarged, exploded, side view of the wiping device illustrated in FIG. 15.

Referring now to FIGS. 15 and 16, there is illustrated a second alternative embodiment of a wiping device generally designated by the reference numeral 300. The wiping device 300 includes a top layer 302 of plastic material such as Trycite and a bottom layer 304 of similar material. The wiping function of the wiping device 300 is performed by a pair of wiping ribs 306 that are formed in the top layer 302 by molding, pressing or other procedures well-known in the art. A pad 308 of blotting paper may be secured to the underside of the top layer 302 behind the wiping ribs 306. The pad of blotting paper 308 is optional and may be included in the wiping device 300 if wiping provided by the wiping ribs 306 is not complete. A slot 310 is cut in the top layer 302, and a reagent pad 312 on a reagent strip 314 extends through the slot 310 and is exposed on the top layer 302 for the application of a body fluid such as blood.

To assemble the wiping device 300, a reagent strip 314 is positioned between the top layer 302 and the bottom layer 304 with the reagent pad 312 extending through the slot 310. The top layer 302 and the bottom layer 304 may be one piece that is folded similar to the procedure of folding the wiping device 200, or the top layer 302 and the bottom layer 304 may be separate pieces that are joined together at the edges maintaining the reagent strip 314 between the top layer 302 and the bottom layer 304.

To use the wiping device 300, a user deposits or applies a body fluid such as blood onto the reagent pad 312. After a predetermined period of time has elapsed, the user grasps the reagent strip 314 and pulls the reagent pad 312 through the slot 310 and between the top layer 302 and the bottom layer 304. Continued pulling of the reagent strip 314 pulls the reagent pad 312 along the wiping ribs 306 spreading the body fluid over the reagent pad 312 and wiping excess body fluid from the top surface of the reagent pad 312. Further blotting or wiping may be provided by the blotting paper 308. Further pulling of the reagent strip 314 completely removes the reagent pad 312 from the wiping device 300. The color of the reagent pad 312 can then be read by an instrument or read visually by the user. Once the reading is completed, the reagent strip 314 and the wiping device 300 can be disposed of to avoid contamination.

Figure 17:
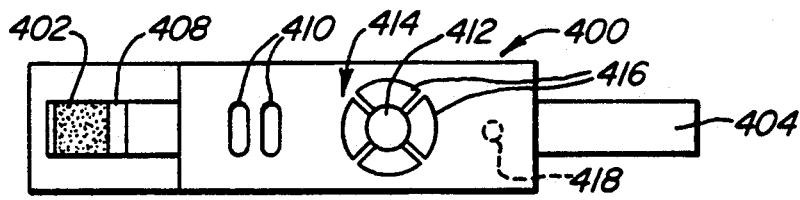
FIG. 17 is a top plan view of a third alternative embodiment of a wiping device with a reagent strip in the ready position.
Figure 18:
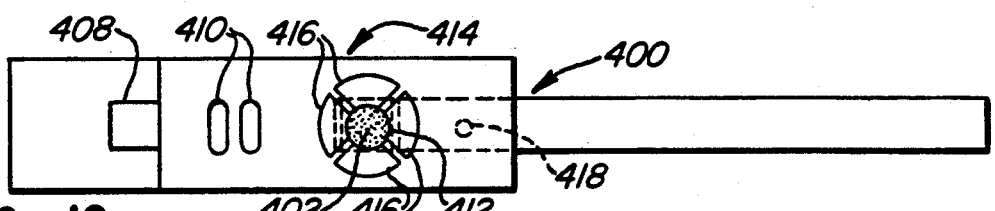
FIG. 18 is a view similar to FIG. 17 with a reagent strip in the read or viewing position.

A third embodiment of a wiping device is illustrated in FIGS. 17 and 18 and is generally designated by the reference numeral 400. The wiping device 400 -functions both to wipe a reagent pad 402 on a reagent strip 404, and to assist a user in matching the color on the reagent pad 402 after deposit of a body fluid and wiping of that pad 402 with a color chart or wheel. The wiping device 400 is self-contained, similar to the wiping devices 200 and 300, and the user is not exposed to the body fluid on the reagent pad 402.

The wiping device 400 is similar to the wiping device 200 in that a sheet of flexible material such as Trycite is folded to form an envelope or jacket 406. The material of the envelope 406 is punched to form a slot 408 through which the reagent pad 402 on the reagent strip 404 extends in the ready position. A pair of wiping ribs 410 are also formed in the upper surface of the envelope 406. The sides and end of the envelope 406 adjacent the reagent pad 402 are sealed at the edges so that the reagent strip 404 can slide back and forth within the envelope 406 without jamming and without too much play.

A viewing aperture or opening 412 is cut in the upper surface of the jacket 406. This aperture or opening 412 is similar to the opening 210 in the wiping device 200 and allows a user or an instrument to read the color on the pad 402 after wiping.

The wiping device 400 differs from the wiping devices discussed earlier in that it is completely self-contained. The wiping device 400 allows a user to compare the color of the reagent pad 402 as viewed through the aperture 412 with a color wheel 414 printed on the envelope 406. The color wheel 414 includes individual segments of preselected colors 416 that correspond to the possible colors of the reagent pad 402 developed in response to a specific level of analyte in the body fluid placed on the reagent pad 402.

To use the wiping device 400, a user deposits a body fluid such as blood on the reagent pad 402. After a predetermined time, the reagent strip 404 is grasped and pulled, moving the reagent pad 402 through the slot 408 and into the envelope 406 (FIG. 18). As the reagent pad 402 passes through the envelope 406, the upper surface of the reagent pad 402 is wiped by wiping ribs 410. The reagent strip 404 is pulled until the reagent pad 402 can be seen through the aperture 412. The color of the reagent pad 402 is then matched with one of the color segments 416 in the color wheel 414. This procedure avoids the need to carry the reagent strip 404 to a matching color chart or similar matching device to compare colors.

To prevent inadvertent withdrawal of the reagent strip 404 from the envelope 406 and also to give the user a definite stop at which point the reagent pad 402 is aligned with the viewing aperture 412, the envelope 406 includes a strip position lock 418 that may be a button or similar bump and a corresponding indention formed in the reagent strip 404. As the reagent strip 404 is pulled out of the envelope 406, the button will align with and move into the corresponding indention in the reagent strip 404. This prevents further inadvertent withdrawal of the reagent strip 404. Once the reagent pad 402 is positioned within the viewing aperture 412, the user may compare the color in the reagent pad 402 with the color segments 416 to determine the level of analytes, such as glucose, in the body fluid. Once this reading is completed, the user may dispose of the entire wiping device 400.

Figure 19:
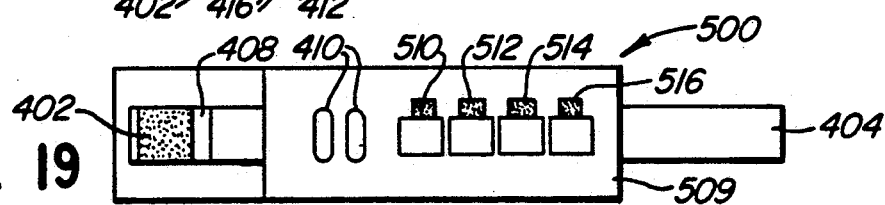
FIG. 19 is a top plan view of a fourth alternative embodiment of a wiping device.

A fourth alternative wiping device is illustrated in FIG. 19 and is generally designated by the reference numeral 500. The wiping device 500 is similar to the wiping device 400 illustrated in FIGS. 17 and 18, and the elements of the wiping device 500 that are identical to the corresponding elements of the wiping device 400 are designated by the same reference numerals as set forth in FIGS. 17 and 18.

The wiping device 500, however, differs from the wiping device 400 in that instead of a single viewing aperture such as the aperture 412, several viewing apertures 502, 504, 506 and 508 are cut into the upper surface of an envelope 509.

Like the wiping device 400, the wiping device 500 is totally self-contained and allows the user to match the color of the reagent pad 402 after wiping with a color segment 510, 512, 514 or 516 printed on the upper surface of the envelope 509 adjacent to the viewing apertures 502, 504, 506 and 508, respectively. Upon pulling the reagent strip 404 and wiping the reagent pad 402 by a pair of wiping ribs 410, the user moves a reagent pad 402 into the viewing aperture 502 to compare the color of the reagent pad 402 with the color segment 510. If the colors do not match, the user pull the reagent strip 404 to position the reagent pad 402 in the viewing aperture 504 adjacent the color segment 512. If the color of the pad 402 does not match the color segment 512, this procedure can be repeated by moving the reagent pad 402 to the viewing aperture 506, and then to the viewing aperture 508, until a color match is obtained informing the user of the level of analyte in the body fluid being tested. Once that determination has been made, the user may dispose of the wiping device 500.

What is claimed and sought in United States Letters Patent is:

1. A device for wiping excess fluid from a test strip, comprising:

a housing having an aperture therethrough, said aperture being dimensioned to allow a test strip inserted therein to be pulled therethrough, and an opening in said housing for the application of fluid directly to the top surface of a test pad of said test strip;

a wiping member extending into said aperture to contact the fluid on said test strip as said test strip passes beneath said wiping member, whereby said wiping member removes excess fluid from said test strip; and said housing further includes a ramp portion which guides said test strip beneath said wiping member, said ramp portion extending upwardly in said housing from a horizontal plane;

wherein said wiping member includes a leading edge and a trailing edge, and wherein said wiping member is angled with respect to the direction of the motion of said test strip to wipe the fluid from the test strip as the test strip passes beneath said wiping member from the leading edge to said trailing edge.

2. The device of claim 1 wherein said wiping member forms an angle of incidence of about 50° with respect to said test strip.

3. The device of claim 1 wherein said housing is fabricated from plastic.

4. The device of claim 1 wherein said wiping member is resilient and flexible.

5. The device of claim 1 which further comprises selected colors affixed to said housing, said selected colors corresponding to colors of said test strip after wiping of fluid from said test strip.

* * * * *